(12) United States Patent
Makihira

(10) Patent No.: US 8,950,863 B2
(45) Date of Patent: Feb. 10, 2015

(54) IMAGE PHOTOGRAPHING APPARATUS AND IMAGE PHOTOGRAPHING METHOD

(75) Inventor: Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/410,566

(22) Filed: Mar. 2, 2012

(65) Prior Publication Data

US 2012/0229765 A1    Sep. 13, 2012

(30) Foreign Application Priority Data

Mar. 10, 2011   (JP) ................. 2011-052297

(51) Int. Cl.
| | |
|---|---|
| A61B 3/14 | (2006.01) |
| G02C 5/20 | (2006.01) |
| A61B 3/00 | (2006.01) |
| A61B 3/10 | (2006.01) |
| G01B 9/02 | (2006.01) |
| A61B 17/00 | (2006.01) |
| G02B 27/00 | (2006.01) |

(52) U.S. Cl.
CPC ............ *A61B 3/102* (2013.01); *G01B 9/02091* (2013.01); *A61B 2017/00216* (2013.01); *G02B 27/0093* (2013.01)
USPC ............................ 351/206; 351/118; 351/246

(58) Field of Classification Search
USPC .......................................... 351/206, 118, 246
See application file for complete search history.

(56) References Cited

U.S. PATENT DOCUMENTS

| | | | |
|---|---|---|---|
| 6,325,512 B1 | 12/2001 | Wei | |
| 7,452,077 B2 | 11/2008 | Meyer et al. | |
| 7,744,221 B2 | 6/2010 | Wei et al. | |
| 7,756,241 B2 | 7/2010 | Mukumoto et al. | |
| 7,789,511 B2 | 9/2010 | Aoki et al. | |
| 2005/0273185 A1* | 12/2005 | Teiwes et al. | 700/44 |
| 2006/0152676 A1* | 7/2006 | Baumann et al. | 351/205 |
| 2006/0228011 A1* | 10/2006 | Everett et al. | 382/128 |
| 2007/0195269 A1 | 8/2007 | Wei et al. | |
| 2008/0055543 A1 | 3/2008 | Meyer et al. | |

(Continued)

FOREIGN PATENT DOCUMENTS

| | | | |
|---|---|---|---|
| CN | 101133943 A | 3/2008 | |
| CN | 101400295 A | 4/2009 | |

(Continued)

OTHER PUBLICATIONS

Jun. 21, 2012 European Search Report in European Patent Appln. No. 12158661.4.

(Continued)

*Primary Examiner* — Scott J Sugarman
*Assistant Examiner* — Mustak Choudhury
(74) *Attorney, Agent, or Firm* — Fitpatrick, Cella, Harper & Scinto

(57) ABSTRACT

An image photographing apparatus includes; an acquiring unit configured to acquire an image of an eye to be inspected, a measuring unit configured to measure movement of the eye to be inspected based on the image, a predicting unit configured to predict the movement of the eye to be inspected based on a cycle of the movement of the eye to be inspected which has been measured by the measuring unit, and a control unit configured to control an acquisition position where the acquiring unit acquires the image based on the movement of the eye to be inspected which has been predicted by the predicting unit.

16 Claims, 12 Drawing Sheets

(56) References Cited

U.S. PATENT DOCUMENTS

| | | |
|---|---|---|
| 2008/0259275 A1 | 10/2008 | Aoki et al. |
| 2009/0060120 A1 | 3/2009 | Mukumoto et al. |
| 2009/0303438 A1* | 12/2009 | Yamada et al. ............ 351/206 |
| 2012/0002166 A1 | 1/2012 | Tomatsu et al. |

FOREIGN PATENT DOCUMENTS

| | | |
|---|---|---|
| EP | 1 602 322 A1 | 12/2005 |
| JP | 2004-512125 A | 4/2004 |
| JP | 2009-072572 A | 4/2009 |
| WO | 2006/105903 A2 | 10/2006 |
| WO | 2009/059034 A1 | 5/2009 |

OTHER PUBLICATIONS

Mar. 27, 2014 Chinese Official Action in Chinese Patent Appln. No. 201210063577.8.

Sep. 28, 2014 Chinese Official Action in Chinese Patent Appln. No. 201210063577.8.

* cited by examiner

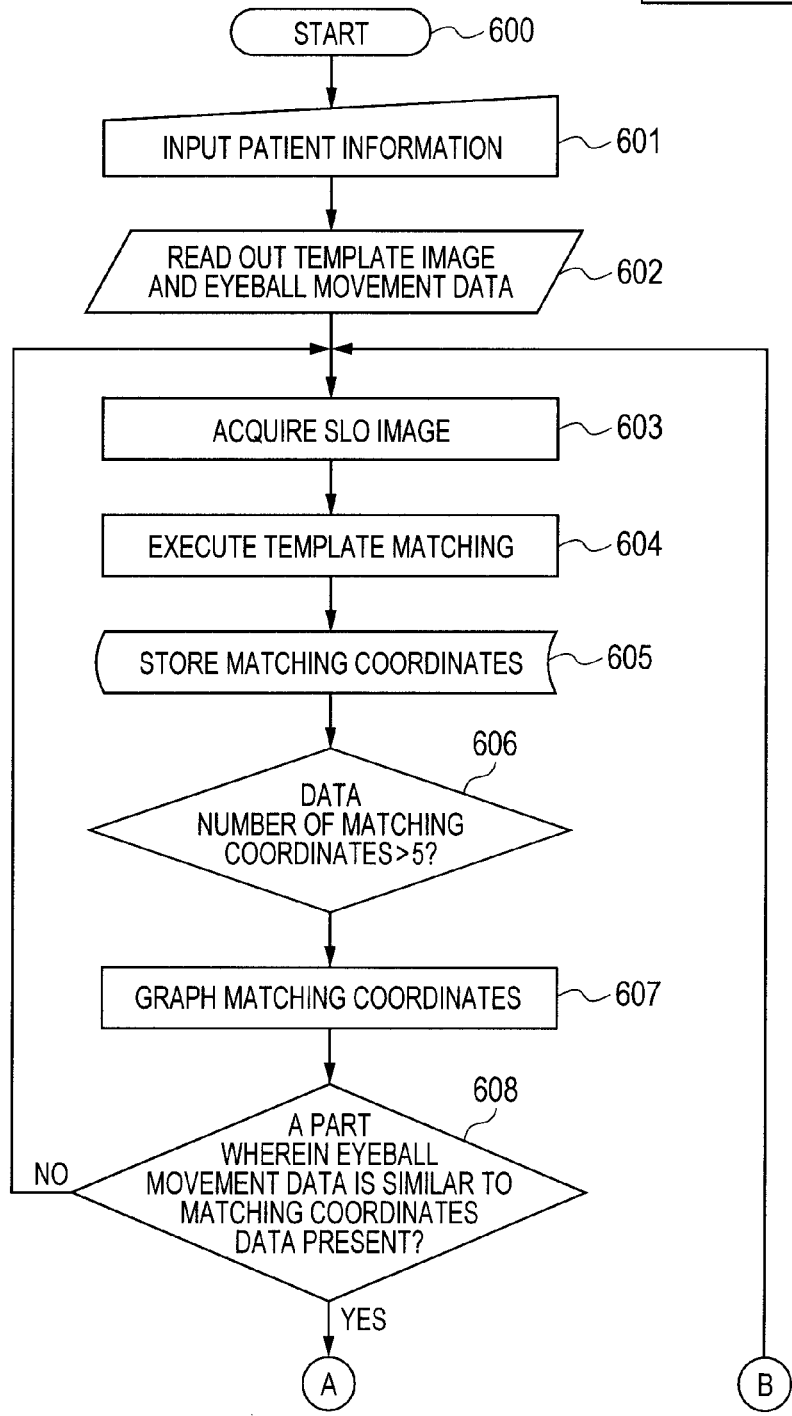

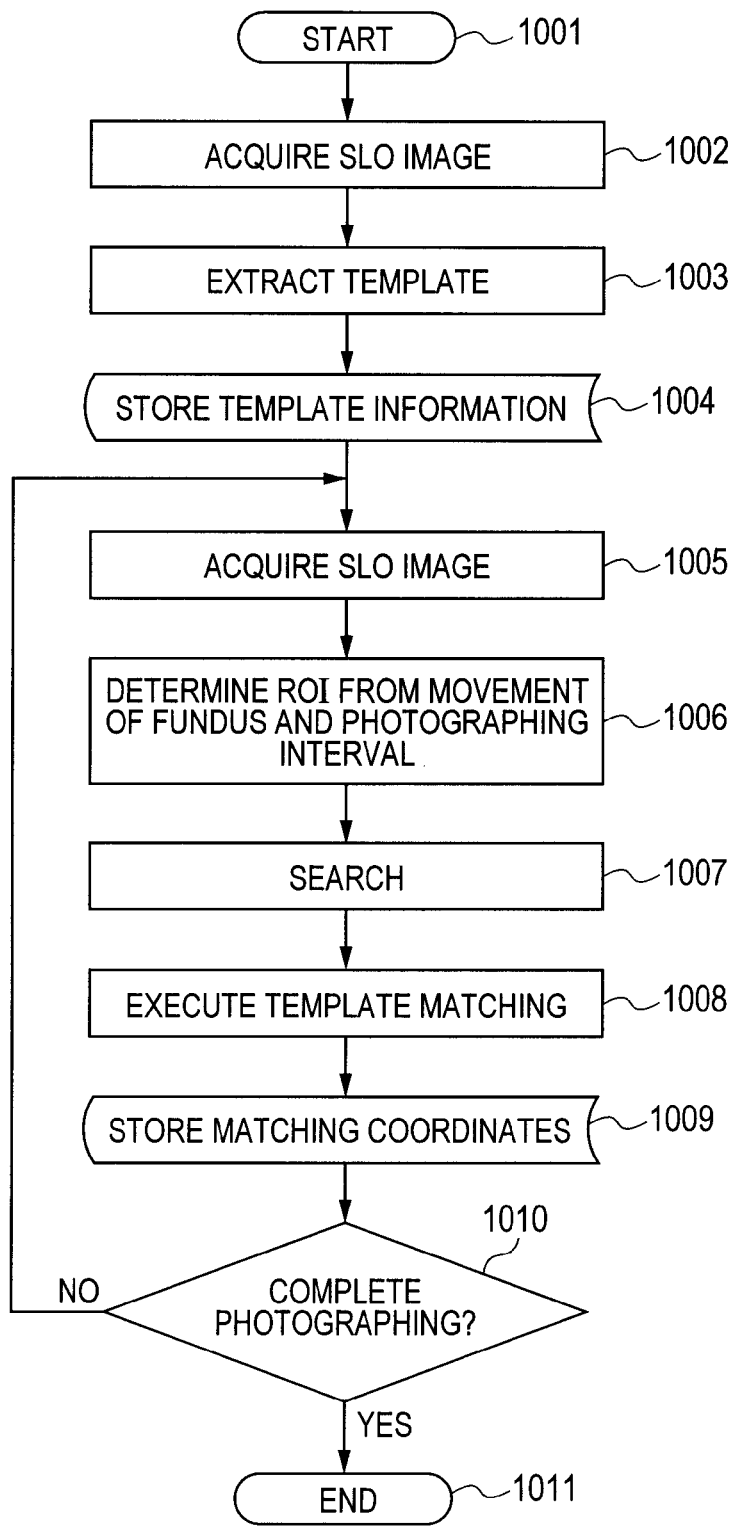

IMAGE PHOTOGRAPHING APPARATUS AND IMAGE PHOTOGRAPHING METHOD

BACKGROUND OF THE INVENTION

1. Field of the Invention

The present invention relates to an image photographing apparatus and an image photographing method. In particular, the present invention relates to an image photographing apparatus and an image photographing method for controllably predicting movement of the eyeball to acquire a predetermined fundus tomographic image.

2. Description of the Related Art

In recent years, OCT (Optical Coherence Tomography) apparatuses that allow fundus tomographic images to be acquired have been attracting attention. A factor in the attention paid to these apparatuses is the capability of enabling noninvasive diagnosis of the internal structure of the ocular fundus, which cannot be observed with other apparatuses. FD-OCT (Fourier Domain OCT), which has demonstrated the capability of high-speed image photographing, dominates the marketplace. The OCT apparatus includes a fundus camera and SLO (Scanning Laser Ophthalmoscopy) installed in the same apparatus to indicate which area of the ocular fundus is to undergo OCT scanning, allowing an OCT image of the vicinity of a predetermined position to be acquired.

On the other hand, in order to allow a microscopic tumor or any abnormalities to be detected during early diagnosis or early medical treatment, photographing timing and positions for OCT images need to be accurately controlled with the movement of the eyeball taken into account.

Japanese Patent Application Laid-Open No. 2004-512125 has been laid open as a patent that takes movement of the eyeball into account.

Japanese Patent Application Laid-Open No. 2009-72572 has been laid open as a patent relating to image photographing timing.

According to Japanese Patent Application Laid-Open No. 2004-512125, an OCT apparatus includes an apparatus for detecting movement of the ocular fundus. The apparatus tracks the optic disc of the ocular fundus and transmits the amount of tracking to an OCT scanner in real time to allow an OCT image of the vicinity of a predetermined position to be acquired.

Furthermore, according to Japanese Patent Application Laid-Open No. 2009-72572, control of an X-ray apparatus is synchronized with the cardiac cycle to allow a predetermined image to be acquired, thus reducing the number of image photographing operations and thus radiation exposure.

The configuration according to Japanese Patent Application Laid-Open No. 2004-512125 requires installation of a special apparatus dedicated to tracking, in addition to a fundus image photographing apparatus or a fundus tomographic image photographing apparatus. This results in the increased size of the apparatus and the need for expensive components such as a scanner for tracking. Another problem is an increase in the number of initial operations such as setting of a target for tracking (the optic disc, described above) and thus in time required for image photographing. Moreover, even with a sophisticated tracking apparatus, the eyeball moves during a process involving detection, calculation and correction, inevitably resulting in time lag.

Japanese Patent Application Laid-Open No. 2009-72572 allows image photographing to be nicely timed but fails to provide control according to independent movement of the fundus plane because the control is based on the cardiac cycle.

SUMMARY OF THE INVENTION

An object of the present invention is to solve the above-described problems and to provide an image photographing apparatus configured to predict the subsequent movement of the eyeball based on movement information about the eyeball to determine control, enabling an image of a predetermined position to be acquired with reduced influence on the movement of the eyeball.

To accomplish this object, an image photographing apparatus according to the present invention includes an acquiring unit configured to acquire an image of an eye to be inspected, a measuring unit configured to measure movement of the eye to be inspected based on the image, a predicting unit configured to predict the movement of the eye to be inspected based on a cycle of the movement of the eye to be inspected which has been measured by the measuring unit, and a control unit configured to control an acquisition position where the acquiring unit acquires the image based on the movement of the eye to be inspected which has been predicted by the predicting unit.

An image photographing method according to the present invention includes acquiring an image of an eye to be inspected, by an acquiring unit, measuring movement of the eye to be inspected based on the image, predicting the movement of the eye to be inspected based on a cycle of the movement of the eye to be inspected which has been measured in the measuring step, and controlling an acquisition position where the acquiring unit acquires the image based on the movement of the eye to be inspected which has been predicted in the predicting step.

The present invention enables the probability of photographing a predetermined position to be improved.

Further features of the present invention will become apparent from the following description of exemplary embodiments with reference to the attached drawings.

BRIEF DESCRIPTION OF THE DRAWINGS

FIG. 10 is a schematic diagram of a control flow according to an exemplary embodiment 3 of the present invention.

DESCRIPTION OF THE EMBODIMENTS

Preferred embodiments of the present invention will now be described in detail in accordance with the accompanying drawings.

Exemplary Embodiment 1

The exemplary embodiment 1 of the present invention will be described.

In the present embodiment, an example in which an OCT image of a predetermined position is acquired will be described. In the example, first, an SLO photographing section acquires an SLO image. Based on the SLO image, the amount of movement in a fundus plane direction is measured. Based on the measured amount of movement of the eye to be inspected, which corresponds to measurement data, the subsequent movement of the ocular fundus is predicted. The result of calculation is reflected in galvano scanners in an OCT photographing section to acquire the OCT image of the predetermined position. The SLO photographing section is illustrated as an aspect of an image photographing unit and a fundus image photographing unit according to the present invention. A unit configured to measure the amount of movement in the fundus planar direction of the eye to be inspected based on the SLO image is illustrated as an area of a CPU 201 described below which functions as a measuring unit. Furthermore, a predicting unit is illustrated as an area of the CPU 201 which functions as the predicting unit; the predicting unit predicts a position that the eye to be inspected is expected to actually reach at a timing for photographing of a fundus image based on the amount of movement of the eye to be inspected which has been measured by the measuring unit. Additionally, the OCT photographing section is illustrated as an aspect of a fundus tomographic image photographing unit according to the present invention. The acquiring unit is formed of either one or both of the OCT photographing section and the fundus image photographing unit in the present invention. By the CPU 201, the OCT photographing section starts OCT photographing at an image acquisition position corresponding to a position reached by the eye to be inspected after movement and predicted by the predicting unit. The SLO photographing section photographs a further fundus image with the position predicted to be reached after movement taken into account. An image photographing operation at the acquisition position is illustrated as an area of the CPU 201 which functions as a control unit configured to control the position where the acquiring unit acquires an image, based on the movement of the eye to be inspected which has been predicted by the predicting unit.

In the exemplary embodiments of the present invention, an eye axis direction is represented as z, a fundus plane horizontal direction is represented as x, and a fundus plane vertical direction is represented as y.

(Configuration of the SLO Photographing Section)

Figure 1:
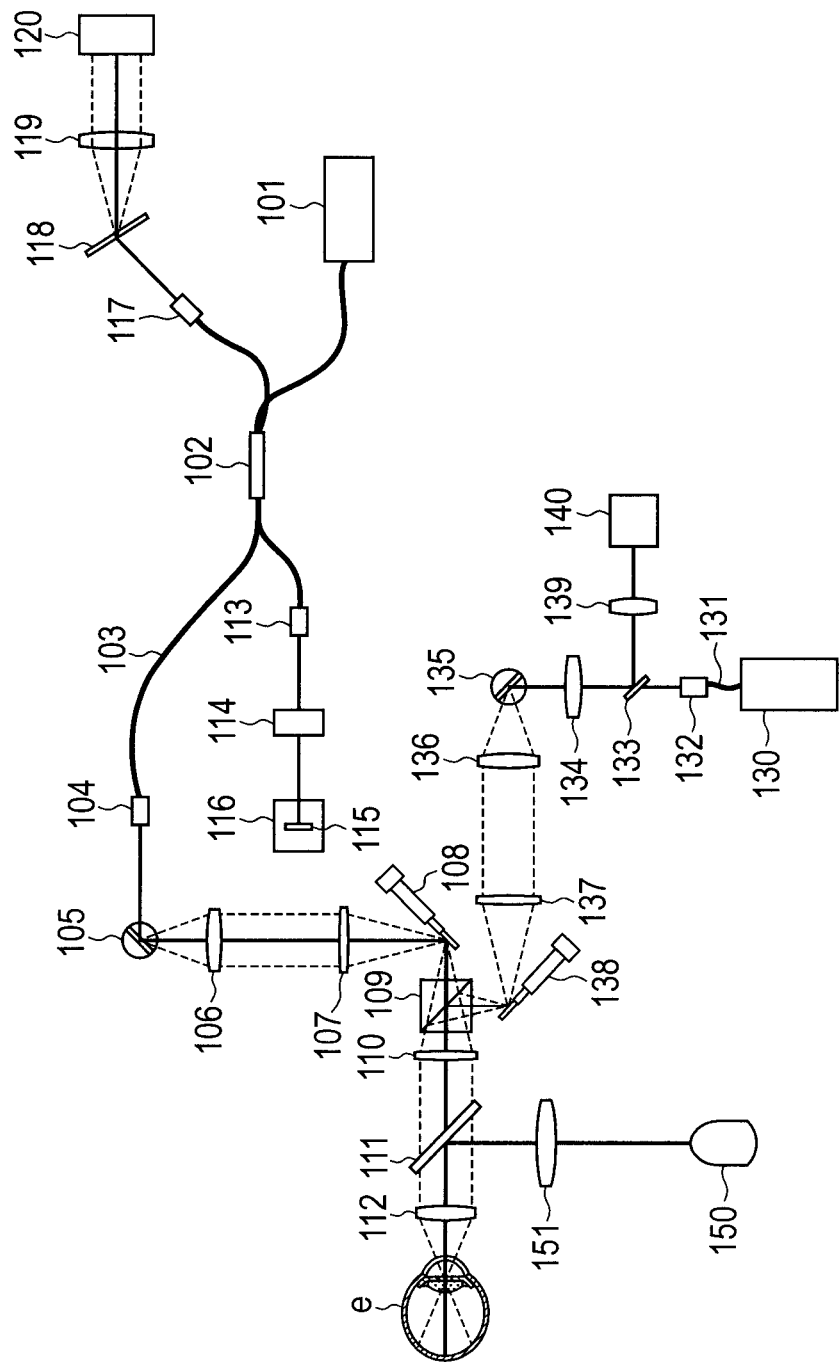
FIG. 1 is a schematic diagram of an optical system in an apparatus according to an exemplary embodiment 1 of the present invention.

The optical configuration of the SLO photographing section configured to acquire a fundus image will be described with reference to FIG. 1. A laser light source 130 may be a semiconductor laser or an SLD (Super Luminescent Diode) light source. A wavelength used for the laser light source 130 is not limited provided that the wavelength can be separated from the wavelength of a low-coherence light source 101 by a dichroic beam splitter 109. However, with the quality of fundus observation images taken into account, a near infrared wavelength range of 700 nm to 1,000 nm may be used. In the present exemplary embodiment, a semiconductor laser with a wavelength of 760 nm is used. Laser beams (SLO beams) emitted from the laser light source 130 exit a fiber collimator 132 as parallel light beams via a fiber 131 and are guided through a perforated mirror 133, a focus lens 134 installed on a focus stage (not shown), and an SLO scanner (Y: the vertical direction in the fundus plane) 135. Then, the light beams travel through lenses 136 and 137 and an SLO scanner (X: the horizontal direction in the fundus plane) 138 and are then reflected by the dichroic beam splitter 109 and enter the eye to be inspected e. The dichroic beam splitter 109 is configured to allow OCT beams described below to pass through, while reflecting SLO beams. Galvano scanners are used as scanners in the SLO photographing section. The SLO beams having entered the eye to be inspected e illuminate the ocular fundus of the eye to be inspected e. The beams are reflected or scattered by the ocular fundus of the eye to be inspected e. The beams then follow the same optical path as described above to return to a ring mirror 133. The position of the ring mirror 133 is conjugate with the position of the pupil of the eye to be inspected e. The beams illuminating the ocular fundus are back-scattered and a portion of the resultant light passes through a peripheral portion of the pupil and is reflected by the ring mirror 133. The portion of the light is formed by a lens 139 into an image on an APD (avalanche photodiode) 140. Based on intensity information in the APD 140, a PC 214 (see FIG. 2) generates a planar image of the ocular fundus (fundus image or SLO image).

(Configuration of the OCT Photographing Section)

The optical configuration of the OCT photographing section will be described with reference to FIG. 1. The low-coherence light source 101 is used as a light source. The light source 101 may be an SLD light source or an ASE (Amplified Spontaneous Emission) light source. For low-coherence light, wavelengths of about 850 nm and about 1,050 nm are suitable for image photographing of the ocular fundus. In the present exemplary embodiment, the SLD light source has a central wavelength of 840 nm and a wavelength half width of 45 nm. Low-coherence light emitted from the low-coherence light source 101 travels through fiber into a fiber coupler 102. The light is then split into measuring light (OCT beam) and reference light. In the present exemplary embodiment, an interferometer configuration using fiber is described. However, the configuration may be a spatial-light optical system using a beam splitter.

The measuring light is emitted from a fiber collimator 104 via fiber 103 as parallel light beams. The parallel light beams travel through an OCT focus lens 121 (not shown) on a focus stage (not shown), an OCT scanner (Y) 105, relay lenses 106 and 107. The light beams further pass through an OCT scanner (X) 108 and the dichroic beam splitter 109 and then through a scan lens 110, a dichroic mirror 111 and an ocular lens 112, and illuminate the eye to be inspected e. Here, galvano scanners are used as scanners (X) 108 and (Y) 105 in an OCT scanning section (corresponding to a scanning unit according to the present invention). The measuring light entering the eye to be inspected e is reflected by the retina and then travels along the same optical path back to the fiber coupler 102. On the other hand, the reference light is guided from the fiber coupler 102 to the fiber collimator 113, where the reference light is converted into parallel light beams, which are then emitted. The emitted reference light passes through a dispersion compensating glass 114 and is reflected by a reference mirror 116 on an optical path length variable stage 115. The reference light reflected by the reference mirror 116 follows the same optical path and returns to the fiber coupler 102.

The measuring light and reference light having returned to the fiber coupler 102 are combined, and the combined light is guided to a fiber collimator 117. Here, the combined light is referred to as interference light. The fiber collimator 117, a transmissive grating 118, a lens 119 and a line sensor 120 form a spectroscope. The spectroscope measures interference light to obtain intensity information for each wavelength. The intensity information for each wavelength measured by the line sensor 120 is transferred to the PC 214, which then is generated as a tomographic image (OCT image) of the eye to be inspected e.

(Internal Fixation Lamp)

In order to stabilize the fixation of the eye, the present exemplary embodiment includes an internal fixation light to be gazed at by the eye to be inspected e. This component corresponds to a fixation unit according to the present invention. As is the case with the OCT photographing section and the SLO photographing section, the internal fixation lamp will be described below with reference to FIG. 1. An internal fixation lamp 150 includes a plurality of light emitting diodes (LD) arranged in a matrix. The PC 214 controllably changes the lighting positions of the light emitting diodes, according to an area to undergo image photographing. The light emitting diodes have a wavelength of 500 nm. Light beams emitted from the internal fixation lamp 150 travel through a lens 151 and the dichroic mirror 111 and illuminate the eye to be inspected e. When the eye to be inspected e gazes at the light beams, a tomographic image of a predetermined position can be photographed. The dichroic mirror 111 is positioned between the scan lens 110 and the ocular lens 112 to separate the light from the fixation lamp (about 500 nm), the OCT beam and the SLO beam (at least 700 nm) from one another in terms of wavelength.

(Unit Configuration and Control)

Figure 2:
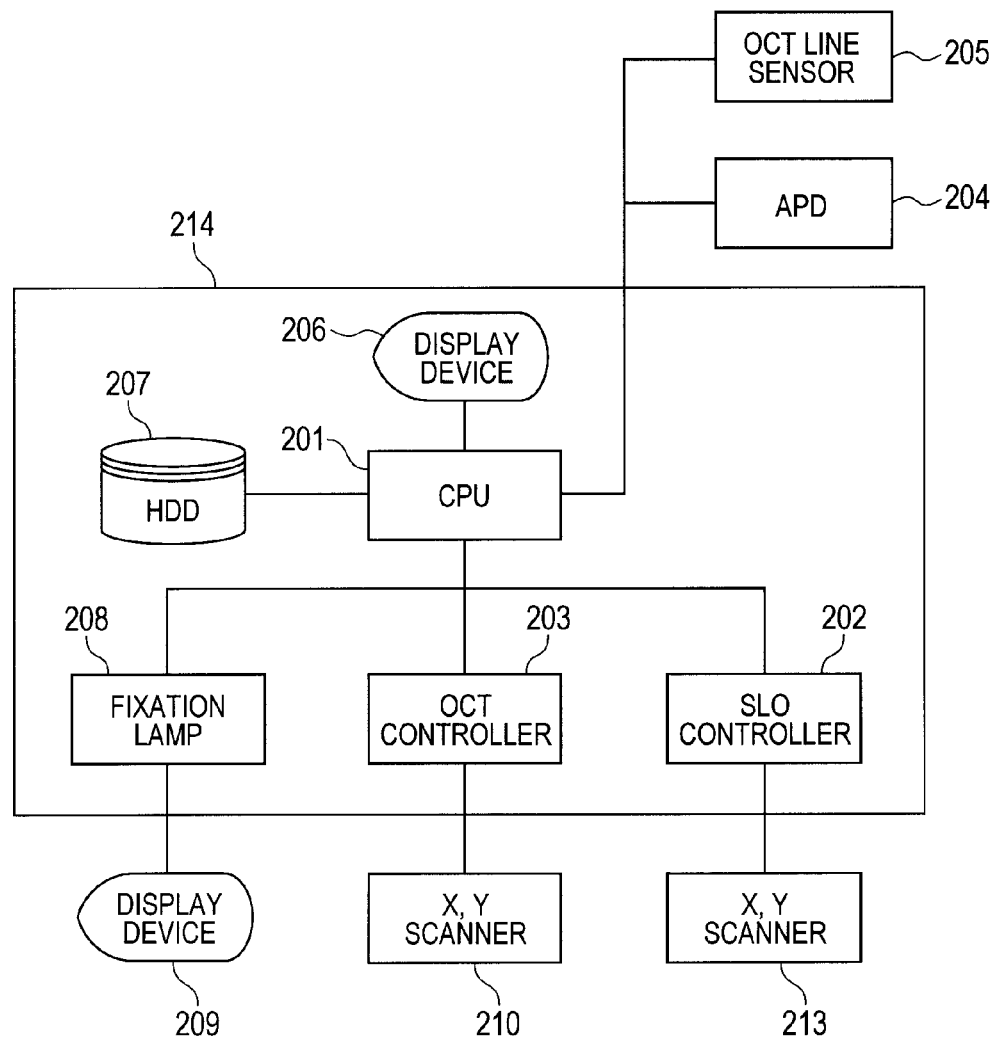
FIG. 2 is a schematic diagram of the functions of the apparatus according to the exemplary embodiment 1 of the present invention.

FIG. 2 illustrates a functional system used in the present exemplary embodiment. The functional system includes a PC 214 including a CPU 201 configured to control the whole system, controllers 202 and 203 configured to control the SLO photographing section and the OCT photographing section, which are main components, a fixation lamp controller 208, an APD 204 (140) including light receiving elements configured to acquire signals for SLO and OCT images, and a line sensor 205 (120); and a display section 206 configured to display a system status and a storing section 207 configured to store fundus images and image photographing conditions.

When the ocular fundus is photographed, the fixation lamp controller 208 controllably displays a lighting position in the internal fixation lamp 150 on a display device 209 (150) so that the eye to be inspected gazes at the lighting position. The CPU 201 provides image photographing conditions to the controllers 202 and 203, which thus drives scanners 210 (105 and 108) and 213 (135 and 138) so that the ocular fundus is scanned by light. Then, light from the ocular fundus reaches the sensors, that is, the APD 204 and the line sensor 205, which transmit electric signals to the CPU 201. The CPU 201 then carries out image processing on the electric signals (to generate an SLO image and an OCT image). The resultant images are displayed on the display section 206, and at the same time or after the display, corresponding information is stored in the storing section 207.

Specific Example

A specific example in which the above-described apparatus is used will be described below.

In the above-described exemplary embodiment, an SLO image of a patient's eye to be inspected is acquired, and a characteristic point is extracted from the image. In the next image, a portion matching the characteristic point is detected by pattern matching, that is, template matching for the characteristic images. Based on changes in the coordinates, movement of the ocular fundus is measured. The pattern matching is executed by an area of the CPU 201 which functions as a pattern matching unit. The result of the measurement is used to predict the subsequent movement of the ocular fundus. An area of the CPU 201 which functions as a control unit controls the galvano scanners of the OCT photographing section based on the prediction. Thus, an OCT image of a predetermined position is acquired. Here, the prediction of the movement according to the present exemplary embodiment is to predict a position reached by the ocular fundus after movement when photographing of the next OCT image is started. The time of prediction depends on intervals at which the apparatus acquires OCT images and the time required for movement measurement.

Figure 3:
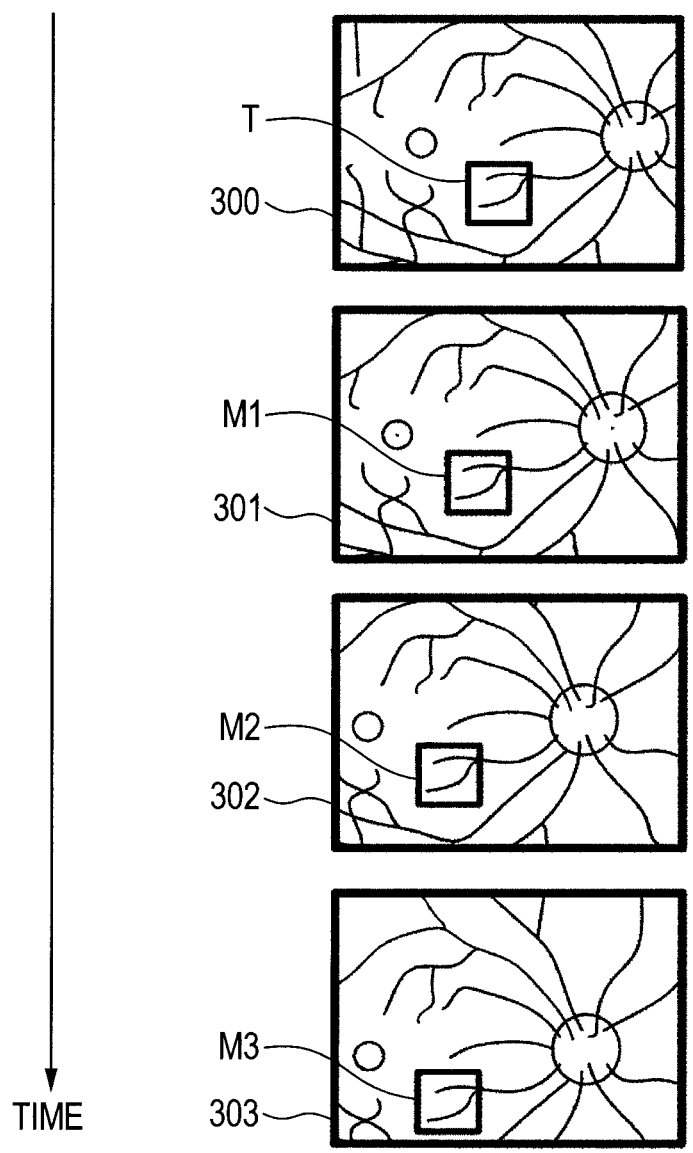
FIG. 3 is a schematic diagram of SLO images acquired when movement of the ocular fundus is measured according to the exemplary embodiment 1 of the present invention.
Figure 4A:
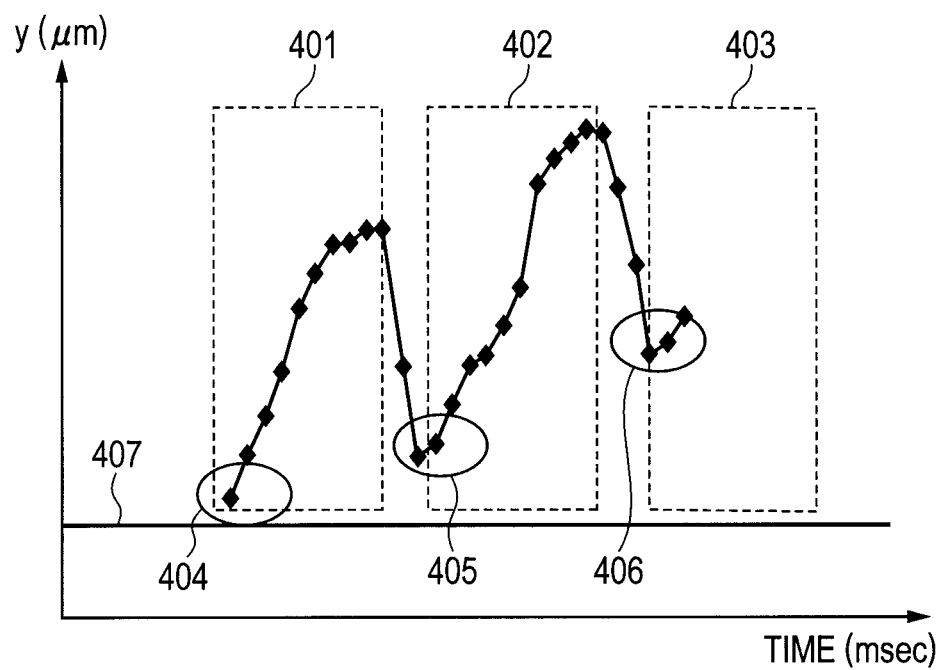
FIGS. 4A and 4B are schematic graphs of coordinates of a template according to the exemplary embodiment 1 of the present invention.
Figure 4B:
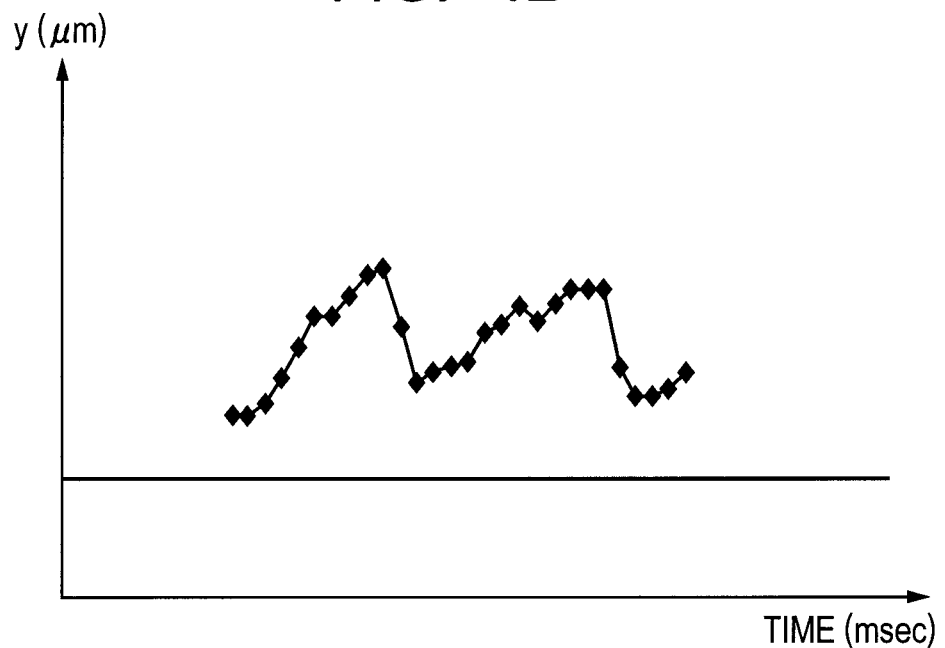

First, a method for measuring the movement of the ocular fundus will be described with reference to FIG. 3. The measurement of movement of the eye to be inspected, which will be described below, is executed by an area of the CPU 201 which functions as the measuring unit. As shown in FIG. 3, the SLO photographing section, serving as the acquiring unit configured to acquire an image of the ocular fundus of the eye to be inspected, is used to acquire a fundus image 300 of the eye to be inspected and extract a characteristic point T (hereinafter referred to as a template image) from the fundus image. Here, the SLO photographing section corresponds to an example of the acquiring unit configured to acquire an image of the eye to be inspected. Information (the image, coordinates and the time of acquisition) about the characteristic point T is stored in the storing section 207. An SLO image 301 newly acquired is searched for the characteristic point T, used for pattern matching with a template image. An area in the fundus image for pattern matching which serves as the characteristic point T is set by an area of the CPU 201 which functions as an area setting unit. An image M1 that matches the characteristic area (the image M1 is hereinafter referred to as a matching image) is detected, and positional information about the matching image M1 is stored. The above-described processing is applied to SLO images 302 and 303 sequentially acquired as shown in FIG. 3. The SLO images 302 and 303 newly acquired are searched for the template image to detect matching images M2 and M3. Information about the matching images M2 and M3 is stored in the storing section 207. Similar steps are repeated to acquire data. The time and coordinates (x, y) serving as positional information are plotted for each of the matching images (FIGS. 4A and 4B). FIG. 4A illustrates the relationship between the time and the movement of the ocular fundus in the direction of the x axis. FIG. 4B illustrates the relationship between the time and the movement of the ocular fundus in the direction of the y axis.

Figure 7:
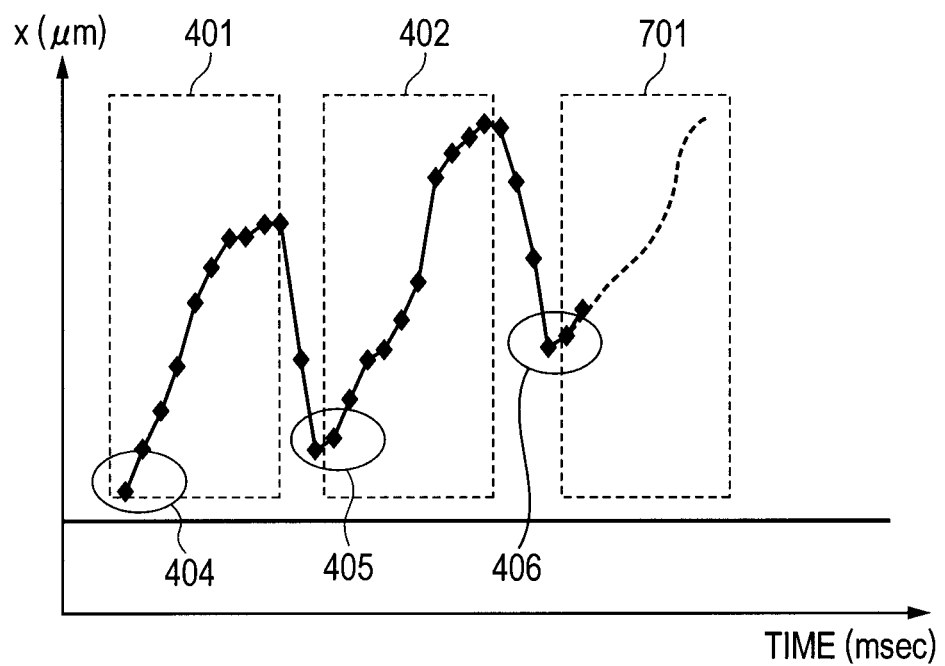
FIG. 7 is a schematic diagram illustrating predicted movement of the ocular fundus according to the exemplary embodiment 1 of the present invention.

Then, based on the acquired results for the movement of the ocular fundus, the movement of the ocular fundus at the time of start of photographing of the next OCT image is predicted. The method for prediction will be described with reference to FIG. 4A. In the prediction according to the present exemplary embodiment, the cycle in which a gazing position returns to the fixation position (407) and the speed at which and the direction in which the gazing position leaves the fixation lamp are calculated and determined based on the plot data. In the graph, shape cycles are calculated as illustrated by 401 and 402. The cycles are indicative of movement in which although the lighting position in the fixation lamp 150 is gazed, drift, that is, slight movement during fixation, causes the gazing position to leave the fixation lamp. Such slight movement during fixation can be considered to be rotation of the eyeball. It has been found that when the eye to be inspected leaves the fixation lamp by at least a given distance, the patient gazes at the fixation lamp again (this corresponds to rapid movement of the ocular fundus between 401 and 402). When the eye to be inspected leaves the fixation lamp 150, the drift continues at a given speed for a given period of time. Utilizing the above-described cycles and characteristics, the movement of the ocular fundus during 406 and the subsequent periods is predicted as illustrated by a dashed line 701 in FIG. 7. The dashed line is obtained by calculating an average value for 401 and 402. The range of data used for the calculation of the average value corresponds to given portions of the graph following 404 and 405, each of which includes a timing and a shape almost similar to those of 406. At the timing 404, the gaze leaves the fixation lamp. At the timing 405, the gaze returns to the fixation lamp and then leaves the fixation lamp. At the timing 406, the gaze also moves back toward the fixation lamp by a certain distance and then starts to move away from the fixation lamp again. Thus, a graph shape is predicted which includes a cycle in which the gaze moves closer to the fixation lamp and a cycle in which the gaze moves away from the fixation lamp. Furthermore, a similar prediction is also applied to the direction of the y axis. That is, the CPU 201 functions as an example of the predicting unit configured to predict the movement of the eye to be inspected based on the cycles of the movement of the eye to be inspected which has been measured by the measuring unit. In the above-described exemplary embodiment, the movement of the eye is predicted using data for two cycles. However, the present invention is not limited to this. Data for at least three cycles or data for one cycle may be used.

After the movement of the ocular fundus is predicted as described above, the result of the prediction is reflected in the control of the galvano scanners of the OCT photographing section. Moreover, the above-described calculation for the prediction deals mainly with saccade and drift of eyeball movement (slight movement during fixation). The eyeball movement includes tremor in which the eyeball moves slightly at high speed (an amplitude of 5 μm and a period of about 100 Hz). According to the present embodiment, in the above-described control of the scanners, vibration with an amplitude of 5 μm and a period of about 100 Hz is taken into account for the above-described prediction, and the galvano scanners are correspondingly controlled to allow an OCT image to be photographed.

Figure 5:
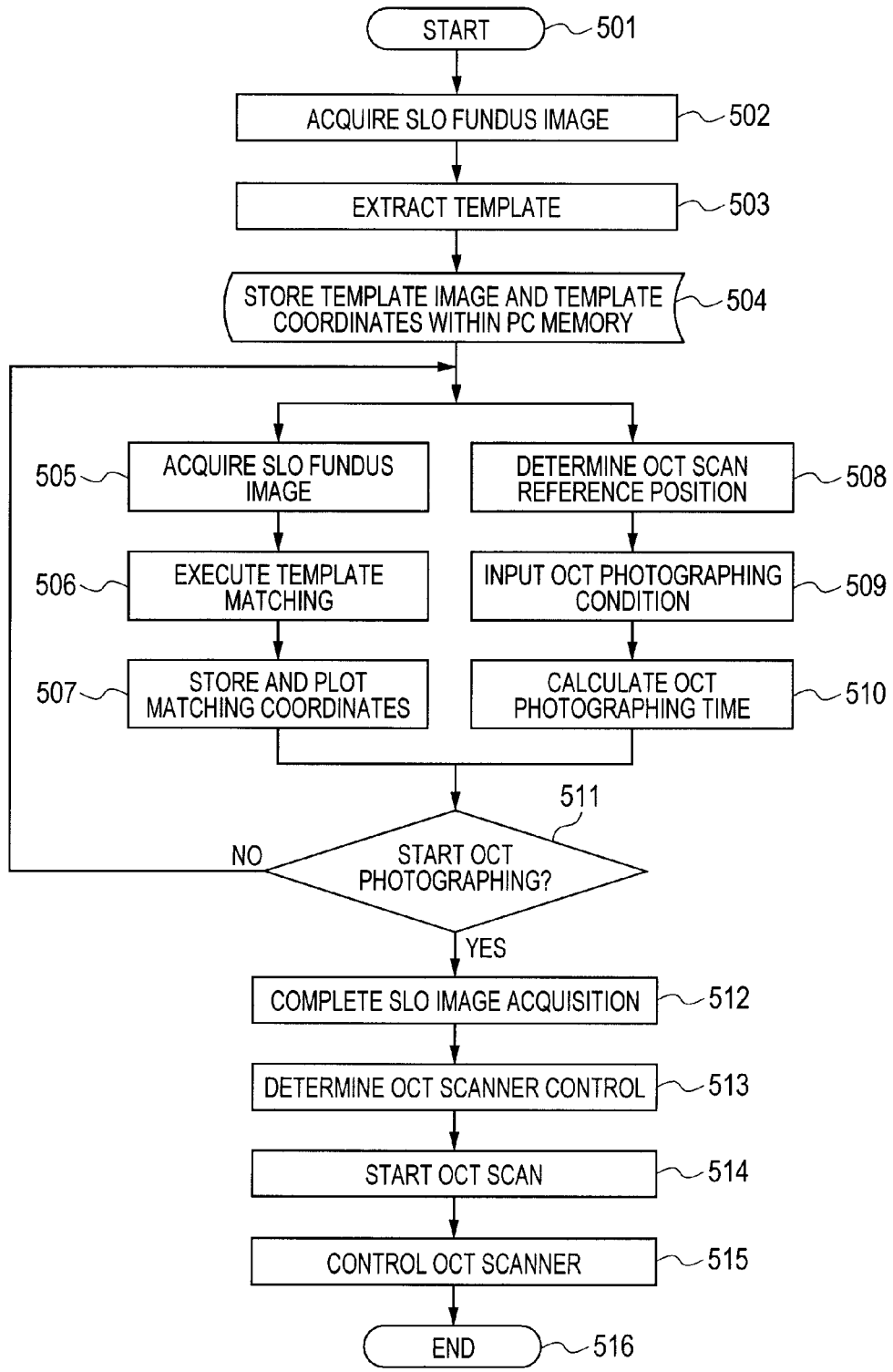
FIG. 5 is a schematic diagram of a control flow according to the exemplary embodiment 1 of the present invention.

The above-described control flow is further described with reference to FIG. 5. Control is started (step 501). The CPU 201 acquires an SLO image (step 502), extracts a template from the SLO image (step 503), and stores the coordinates of the template in the storing section 207 (step 504). The CPU 201 acquires the next SLO image (step 505), executes template matching (step 506), and measures the coordinates of the matching image. The above-described steps correspond to a measuring step according to the present invention. Then, the results of the measurement are stored in the storing section 207, and at the same time, plotted as described above (step 507). During steps 505 to 507, based on the examiner's instruction, an OCT scan position is determined (step 508), other OCT photographing conditions are accepted (step 509), and the time of OCT photographing is calculated (step 510).

Once preparations for image photographing are completed, OCT photographing is started (step 511). In response to an instruction in step 511, the acquisition of SLO images is stopped (step 512), and the subsequent movement of the ocular fundus, that is, OCT scanner control, is determined based on plot information including the matching coordinates (step 513). The above-described steps correspond to a predicting step according to the present invention. After the scanner control is determined, an image photographing step is executed; an OCT scan is started (step 514) and an OCT image is acquired (step 515).

Figure 8:
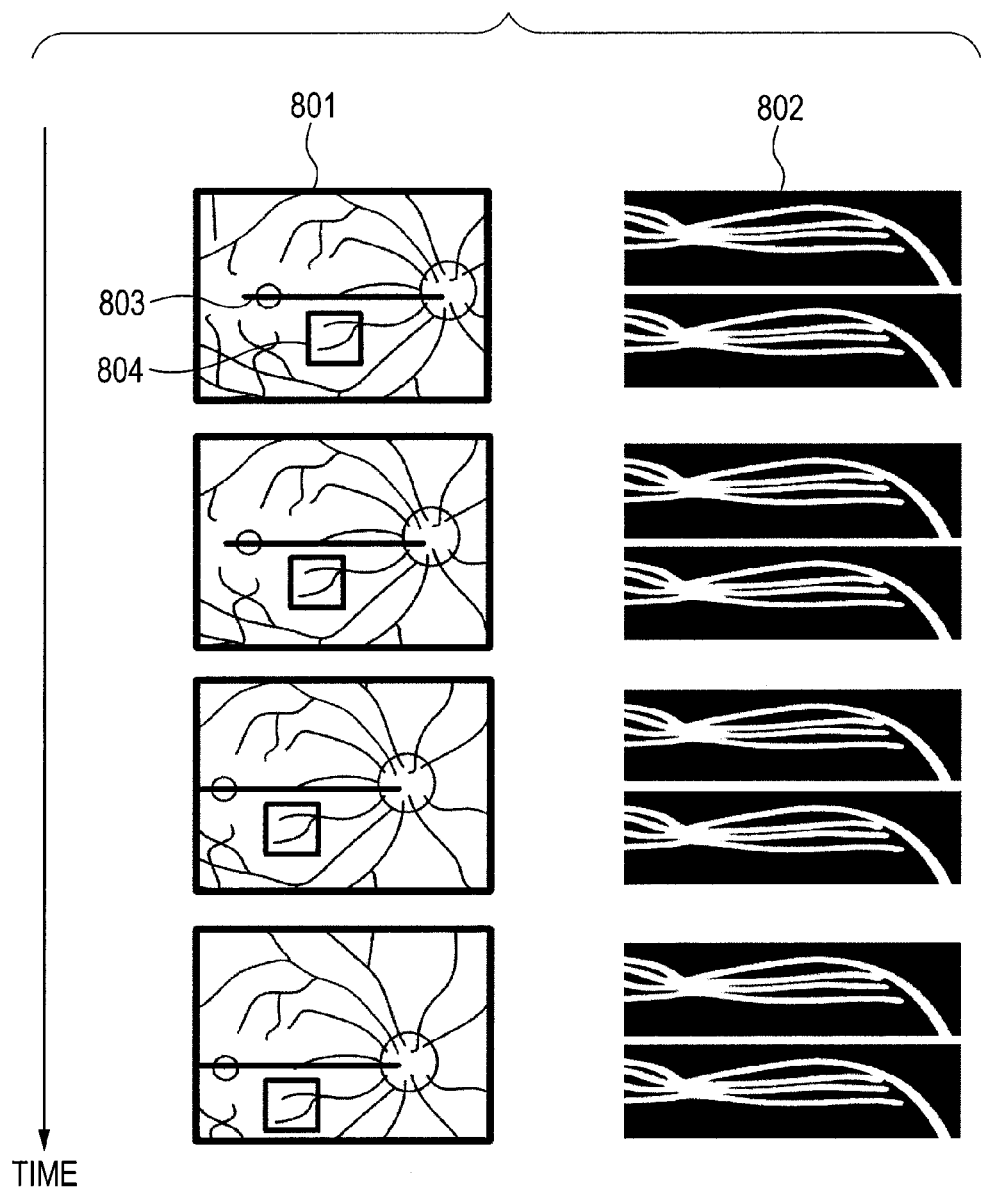
FIG. 8 is a schematic diagram of SLO images and OCT images according to the exemplary embodiment 1 of the present invention.

FIG. 8 illustrates the results of a process of detecting the movement of the ocular fundus in SLO images, determining the control of the scanner of the OCT photographing section based on the movement of the ocular fundus, and driving the scanner under the determined control to acquire OCT images. The SLO images are shown at 801, the OCT images are shown at 802, the OCT scan position is shown at 803, and the template position is shown at 804. The galvano scanners of the OCT photographing section are driven according to the predicted movement of the ocular fundus. Thus, the OCT scan position remains unchanged with respect to the ocular fundus, and similar OCT images are stably acquired.

The above-described control allows an OCT image of a predetermined fundus position to be acquired.

That is, the present invention includes the measuring unit in the CPU 201 which measures the movement of the eye to be inspected, the image photographing unit including the OCT photographing section or SLO photographing section configured to photograph a fundus image of the eye to be inspected, the control unit in the CPU 201 which controls the image photographing position where the image photographing unit photographs a fundus image, and the predicting unit configured to predict the movement of the eye to be inspected. The control unit controls the image photographing unit so as to prevent the image photographing position in the eye to be inspected from varying, based on the predicted movement of the eye to be inspected. The term "predicted movement" as used herein refers to the difference between the position where the characteristic point is present at the timing of the image photographing and the position of the characteristic point on which the prediction is based. The variation in image photographing position corresponds to a positional shift, based on the difference, of the center of image photographing or the position where a scan with the measuring light is started.

Exemplary Embodiment 2

In the present exemplary embodiment, an example will be described in which predictive control is performed using past data, to acquire OCT images of a predetermined position and in which during OCT photographing, SLO images are checked for the movement of the ocular fundus at a given period.

The configuration of the apparatus (SLO photographing section and OCT photographing section) and controller used in the present exemplary embodiment is the same as in the exemplary embodiment 1 and thus description thereof will be omitted.

Specific Example

Figure 9A:
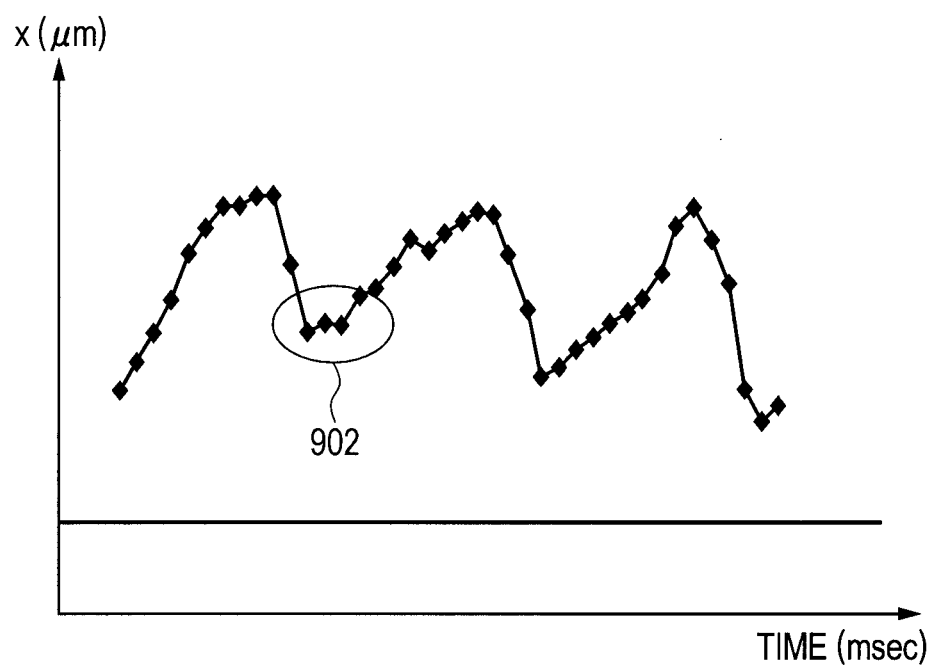
FIGS. 9A and 9B are schematic graphs illustrating predictive control according to the exemplary embodiment 2 of the present invention.
Figure 9B:
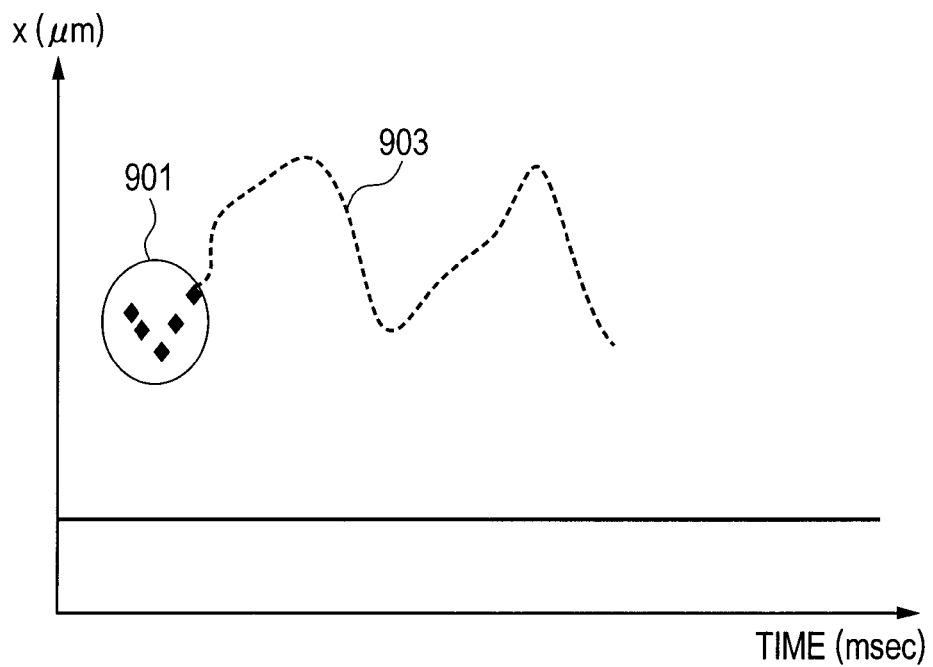

In the present exemplary embodiment, data about the movement of the ocular fundus is already present (information about the patient) and is read out from the storing section 207 of the PC 214 (FIG. 9A). The storing section 207 corresponds to the storing unit according to the present invention, and stores measured data. Then, as is the case with the exemplary embodiment 1, the SLO photographing section is used to photograph the ocular fundus to acquire a plurality of fundus images, and the movement of the ocular fundus is measured (FIG. 9B).

Then, based on the read-out movement of the ocular fundus and the measured movement, a matching point is found and the movement of the ocular fundus is predicted. The method for prediction will be described with reference to FIGS. 9A and 9B. The graph shape in FIG. 9A is searched for a measured shape illustrated at 901 in FIG. 9B to detect a point with the highest degree of matching (902 in FIG. 9A). The degree of matching is determined with the distance from the fixation lamp and the corresponding graph shape taken into account. The above-described operation is performed by an area of the CPU 201 which functions as a unit configured to determine the difference between the lighting position in the fixation lamp serving as the fixation unit and the fixation position in the eye to be inspected. The predicting unit uses the difference to predict the movement of the ocular fundus. Based on the movement of the ocular fundus subsequent to the point with the highest degree of matching, the control of the galvano scanners of the OCT photographing section is determined. The galvano scanners are controlled based on a graph shape corresponding to the following characteristics of the eye: for example, after the V shape illustrated at 901, the gaze moves away from the fixation lamp at a constant speed, and when the gaze reaches a certain distance from the fixation lamp, returns to the position of the fixation lamp. That is, a portion of the past data which is indicative of a V shape is set to be a reference shape, and the current data is searched for a portion matching the reference shape at a high degree. If such a portion is found, the galvano scanners are controlled according to the past movement of the eye.

In the present exemplary embodiment, even during OCT photographing, SLO images are actually acquired, and the amount of movement of the fundus is measured. Then, the difference between the position scanned by the OCT galvano scanners and the amount of movement is calculated to monitor a deviation in real time. These steps are executed by a calculating unit included in the measuring unit to calculate the difference between the image photographing position acquired by the image photographing unit including one of the SLO photographing section and the OCT photographing section and the image photographing position after the movement of the eye to be inspected which has been predicted by the predicting unit.

Figure 6B:
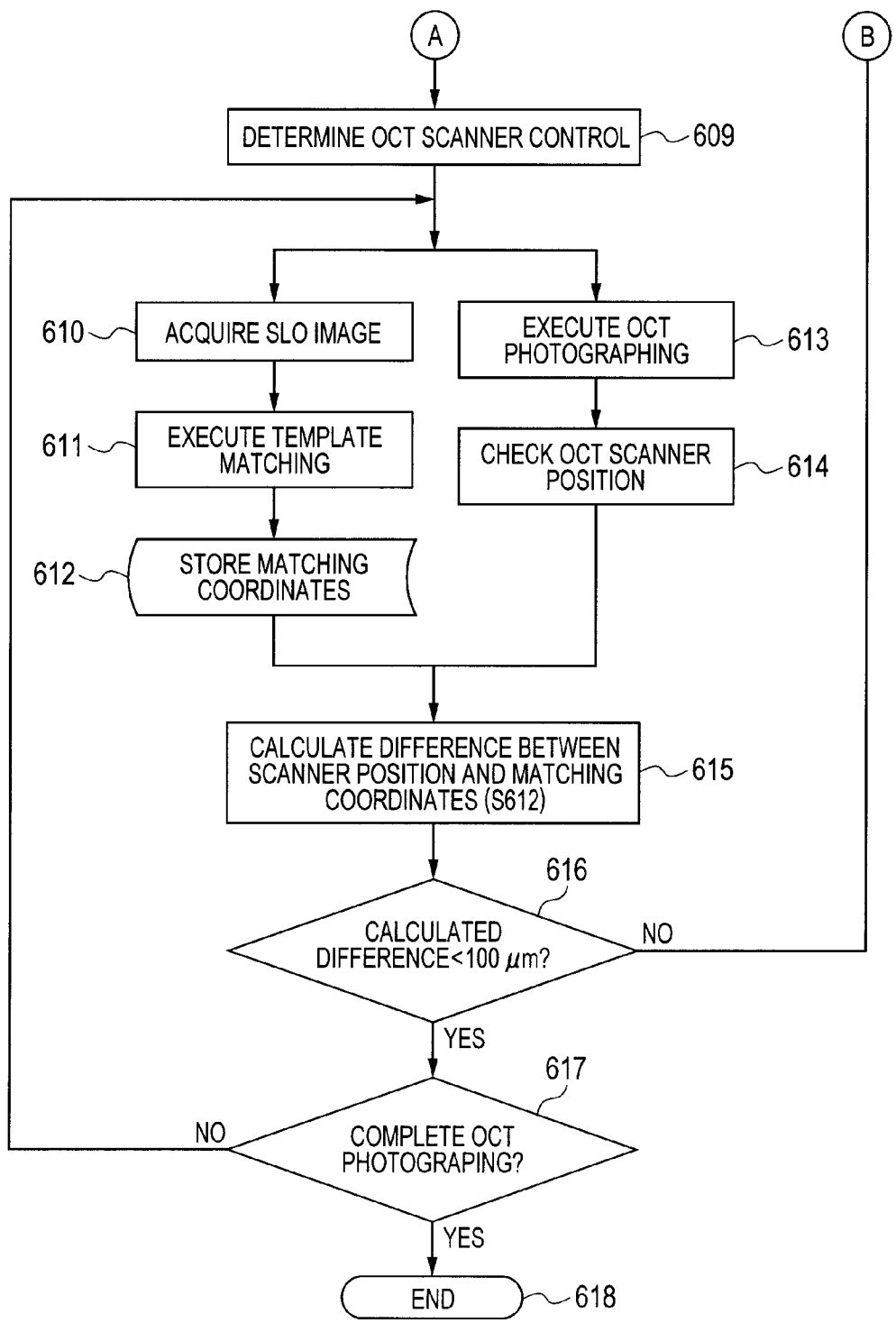
FIG. 6 is comprised of FIGS. 6A and 6B showing schematic diagrams of a control flow according to an exemplary embodiment 2 of the present invention.

The flow according to the present exemplary embodiment will be described with reference to FIGS. 6A and 6B. The CPU 201 accepts input patient information (step 601), and reads out a template image previously acquired and data about the movement of the eyeball, from the storing section 207 (step 602). Then, a fundus SLO image of the eye to be inspected is acquired using the SLO photographing section (step 603), template matching is executed using the template image (step 604), and matching coordinates are stored (step 605). After at least five sets of matching coordinates are acquired (step 606), the positional information of the coordinates is graphed (step 607). The past data about the movement of the eyeball and the graph in step 607 are searched for points with similar movements of the eyeball (step 608). Based on the similar points, the control of the OCT scanner is determined with the movement of the eyeball taken into account (step 609). Subsequently, SLO images continue to be acquired (step 610), template matching is executed (step 611), and matching coordinates are stored (step 612). Simultaneously with steps 610 to 612, the OCT galvano scanners are controlled according to the control in step 609 to execute image photographing (step 613). The positions of the galvano scanners are detected for every image photographing (step 614). The positions of the scanners of the OCT photographing section are compared with the matching coordinates in step 612 to calculate the difference between the position and the coordinates (step 615). When the difference is, for example, at least 100 µm (step 616), there is a difference between the actual movement of the ocular fundus and the control of the galvano scanners, preventing the predetermined position from being achieved. The process thus returns to step 602 for re-setting. When the difference is smaller than 100 µm, the apparatus checks whether the OCT photographing section has completed image photographing (step 617). The processing is then completed.

The present exemplary embodiment uses the past data to enable the movement of the ocular fundus to be easily predicted through calculations, thus allowing an OCT image of the predetermined position to be acquired. The predicted value and the measured value are checked in real time to improve the accuracy of the measurement.

In the above-described exemplary embodiment, the position of the scanner of the OCT photographing section is compared with the matching coordinates in step 612 to calculate the difference between the position and the coordinates. However, the present invention is not limited to this. For example, the calculation of the difference may be omitted. That is, steps 613 to 616 in FIGS. 6A and 6B may be omitted.

Furthermore, in the above-described exemplary embodiment, the galvano scanners are controlled based on the past data about the movement of the eye. However, the information required to control the galvano scanners is not limited to this data. For example, the past data about the movement of the eye may be the average of a plurality of measured values for the movement of the eye or the data about the movement of the eye resulting from only one measuring operation. Here, averaging a plurality of measured values for the movement of the eye allows reliable data to be acquired and enables the movement of the eye to be inspected to be accurately predicted. Alternatively, the past data about the movement of the eye may be the average of data about the movement of the eye for a plurality of patients. For example, the movement of the eye varies with age, and thus data may be acquired which concerns the movement of the eye for patients in some age groups, for example, patients in their 20s and 30s. In this case, the data about the movement of the eye used may be determined depending on the patient's age. Additionally, data about the movement of the eye may be averaged by age group and by sex. The use of such data enables the movement of the eye to be predicted even for a new patient to allow the galvano scanners to be properly controlled.

Alternatively, as data to be used, the examiner may select one from the group consisting of the average of a plurality of measured values for the movement of the eye, data about the movement of the eye resulting from only one measuring operation, the average for the movement of the eye calculated for each age group of the patients, and the average for the movement of the eye calculated for each age group of the patients and for each sex of the patients. For example, before step 602 in FIGS. 6A and 6B, a screen may be displayed on the display device 206 so that the examiner can select data used on the screen. This allows the examiner to flexibly select data used to predict the movement of the eye, according to the patient, thus enabling the movement of the eye to be more accurately predicted.

Exemplary Embodiment 3

In the present exemplary embodiment, an example will be described in which the measurement speed of movement of the ocular fundus is increased when the difference is calculated in real time as is the case with the exemplary embodiment 2, thus preventing a possible significant difference. The description of the SLO photographing section, the OCT photographing section, the control function and the method for calculating predicted data is similar to the exemplary embodiments 1 and 2, and is thus omitted.

In connection with an example in which data about the predicted movement of the ocular fundus is reflected in a search area for template matching (hereinafter referred to as an ROI) to allow the ROI to be narrowed, thus increasing the measurement speed, the control step will be described with reference to FIG. 10.

The CPU 201 acquires an SLO image (step 1002), and extracts a template from the SLO image (step 1003). The CPU 201 stores the extracted template information in the storing section 207 (step 1004). The CPU 201 acquires a new SLO image (step 1005), and determines a search area in the acquired SLO image based on data about the predicted movement of the ocular fundus and the frame rate of the SLO image (step 1006). The CPU 201 searches the determined area (step 1007), and detects a matching image (step 1008). The CPU 201 then stores information about the matching image (step 1009). The CPU 201 checks whether image photographing of the ocular fundus has been completed (step 1010), and completes the process. Based on the results obtained (coordinate information), the CPU 201 measures the movement of the ocular fundus. Step 1006 corresponds to processing specific to the present exemplary embodiment.

Figure 11:
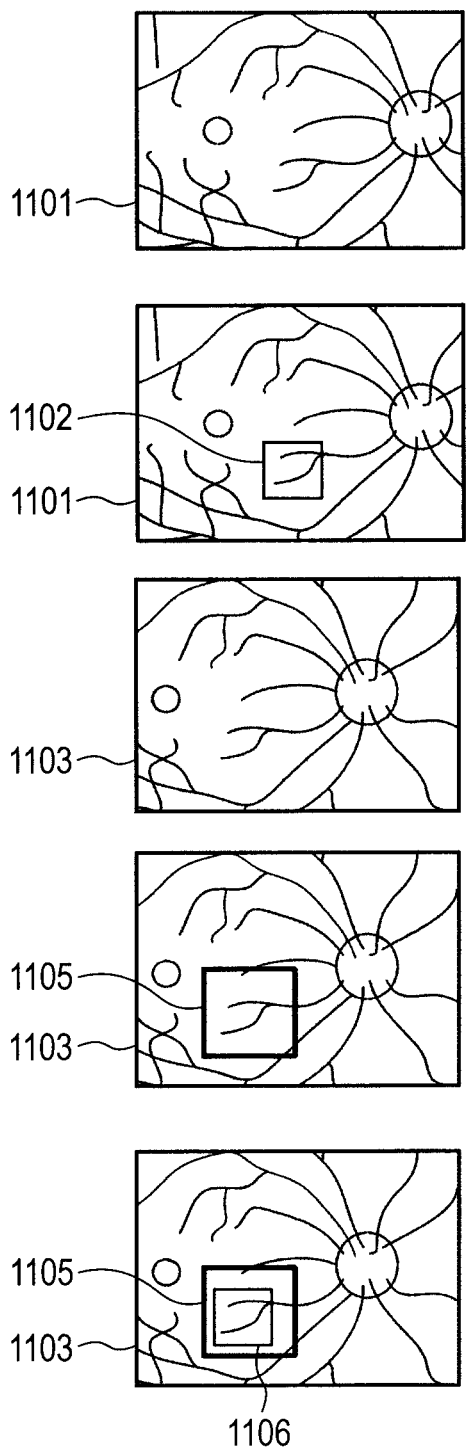
FIG. 11 is a schematic diagram illustrating template matching according to the exemplary embodiment 3 of the present invention.

The above-described steps will be described below with reference to images actually acquired (FIG. 11).

The CPU 201 acquires an SLO image 1101 (step 1002), and extracts a template 1102 from the SLO image (step 1003). The CPU 201 acquires a new SLO image 1103 (step 1005), and determines a search area 1105 in the SLO image acquired (step 1006). The CPU 201 searches the determined area 1105 (step 1007) to detect a matching image 1106 (step 1008).

As described above, in template matching, when data about the predicted movement of the ocular fundus is reflected in the determination of an ROI. This allows the ROI to be narrowed to reduce the matching time, further preventing possible mismatching.

Another Exemplary Embodiment 1

In the exemplary embodiments 1 and 2, predictive control is reflected in the galvano scanners of the OCT photographing section. However, the OCT apparatus may be replaced with an SLO apparatus. Furthermore, the SLO photographing section detects the movement of the ocular fundus. However, similar effects can be exerted by LSLO (Line-LSO) or any other method. Such a method may involve an apparatus configured to detect the movement of the ocular fundus (or the movement of the eyeball) at high speed (the method may include a Purkinje effect, Limbus tracking and a search coil).

The method for predicting the movement of the ocular fundus may use any other calculation including a simple calculation such as a calculation of an approximation curve from each point of the plot or a calculation based on a linear least-squares method.

Measurement can be achieved with errors minimized by acquiring an OCT image at the same timing when the patient gazes at the fixation lamp (404 and 405 in FIG. 4A). Furthermore, the timing for image photographing may be after the end of saccade. Since the saccade is not a continuous movement, an OCT image at a predetermined position can be acquired by executing image photographing between saccade cycles.

Saccade, drift and tremor depend on the examiner, and thus each parameter, particularly for tremor (5 µm, 10 Hz), may be controlled to an appropriate value.

In the exemplary embodiments 1 and 2, the internal fixation lamp is used as a fixation lamp. However, an external fixation lamp may be used.

Another Exemplary Embodiment 2

The present invention is not limited to the above-described exemplary embodiments, but many variations may be made to the exemplary embodiments without departing from the spirits of the exemplary embodiments. For example, the above-described exemplary embodiments have been described in conjunction with the movement of the ocular fundus. However, the present invention is not limited to this but is applicable to the anterior eye part.

Furthermore, the present invention is implemented by executing the following processing. That is, software (program) configured to implement the functions of the above-described exemplary embodiments is supplied to one of a system and an apparatus via one of a network and any of various storage media. A computer (or a CPU or an MPU) in the system or the apparatus then reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-052297, filed Mar. 10, 2011, which is hereby incorporated by reference herein in its entirety.

What is claimed is:

1. An image photographing apparatus comprising:
a measuring unit for measuring a movement of an eye to be inspected;
an acquiring unit for acquiring an image of a fundus of the eye to be inspected;
a control unit for controlling an acquiring position of the acquiring unit at a time of acquiring the image of the fundus; and
a predicting unit for predicting the movement of the eye to be inspected based on a periodical movement of the eye to be inspected with respect to a fixation target, which movement has been measured by the measuring unit,
wherein the control unit controls the acquiring position based on the movement of the eye to be inspected which has been predicted by the predicting unit,
wherein the movement of the eye to be inspected with respect to the fixation target includes (a) a leaving movement in which a gazing position of the eye to be inspected leaves from the fixation target and (b) a returning movement in which the gazing position returns to the fixation target, and wherein the predicting unit predicts the movement of the eye to be inspected based on the leaving movement and the returning movement.

2. The image photographing apparatus according to claim 1, wherein the acquiring unit is one of (a) a fundus tomographic image photographing unit configured to photograph a tomographic image of the eye to be inspected and (b) a fundus image photographing unit configured to photograph a planar image of the eye to be inspected.

3. The image photographing apparatus according to claim 2, further comprising a storing unit configured to store measured data about the movement of the eye to be inspected,
wherein the predicting unit is configured to predict the movement of the eye to be inspected using (a) the movement with respect to the fixation target and (b) the measured data stored in the storing unit.

4. The image photographing apparatus according to claim 1, wherein the measuring unit comprises a fundus image photographing unit configured to photograph a fundus image of the eye to be inspected, and measures the movement of the eye to be inspected based on a plurality of fundus images photographed by the fundus image photographing unit.

5. The image photographing apparatus according to claim 4, wherein the measuring unit measures the movement of the eye to be inspected by executing pattern matching on the plurality of fundus images.

6. The image photographing apparatus according to claim 5, wherein the measuring unit further comprises an area setting unit configured to set an area of the fundus image to undergo pattern matching.

7. The image photographing apparatus according to claim 4, further comprising a storing unit configured to store measured data about the movement of the eye to be inspected,
wherein the predicting unit is configured to predict the movement of the eye to be inspected using (a) the movement with respect to the fixation target and (b) the measured data stored in the storing unit.

8. The image photographing apparatus according to claim 1, further comprising a storing unit configured to store measured data about the movement of the eye to be inspected,
wherein the predicting unit is configured to predict the movement of the eye to be inspected using (a) the movement with respect to the fixation target and (b) the measured data stored in the storing unit.

9. The image photographing apparatus according to claim 1, wherein the measuring unit measures rotation of an eyeball.

10. The image photographing apparatus according to claim 1, further comprising a fixation unit configured to stabilize fixation of the eye to be inspected.

11. The image photographing apparatus according to claim 10, further comprising a determining unit configured to determine a difference between a lighting position in the fixation unit and a fixation position at which the eye to be inspected is fixed,
wherein the predicting unit uses the difference for the prediction.

12. The image photographing apparatus according to claim 1, wherein the measuring unit further comprises a calculating unit configured to calculate a difference between the predicted position and the acquiring position where the acquiring unit acquires the image.

13. The image photographing apparatus according to claim 1, wherein the measuring unit determines a cycle of the movement of the eye to be inspected, and the predicting unit predicts the movement of the eye to be inspected based on the cycle.

14. An image photographing method comprising:
measuring a movement of an eye to be inspected;
acquiring an image of a fundus of the eye to be inspected, by an acquiring unit;
controlling an acquiring position of the acquiring step at a time of acquiring the image of the fundus; and
predicting the movement of the eye to be inspected based on a periodical movement of the eye to be inspected with respect to a fixation target, which movement which has been measured in the measuring step,
wherein the controlling step controls the acquiring position based on the movement of the eye to be inspected which has been predicted,
wherein the movement of the eye to be inspected with respect to the fixation target includes (a) a leaving movement in which a gazing position of the eye to be inspected leaves from the fixation target and (b) a returning movement in which the gazing position returns to the fixation target, and
wherein the predicting step predicts the movement of the eye to be inspected based on the leaving movement and the returning movement.

15. A non-transitory computer-readable recording medium that records a program which causes a computer to execute the respective steps of an image photographing method comprising:
measuring a movement of an eye to be inspected;
acquiring an image of a fundus of the eye to be inspected, by an acquiring unit;
controlling an acquiring position of the acquiring step at a time of acquiring the image of the fundus; and
predicting the movement of the eye to be inspected based on a periodical movement of the eye to be inspected with respect to a fixation target, which movement has been measured in the measuring step,
wherein the controlling step controls the acquiring position based on the movement of the eye to be inspected which has been predicted,
wherein the movement of the eye to be inspected with respect to the fixation target includes (a) a leaving movement in which a gazing position of the eye to be inspected leaves from the fixation target and (b) a returning movement in which the gazing position returns to the fixation target, and
wherein the predicting step predicts the movement of the eye to be inspected based on the leaving movement and the returning movement.

16. An apparatus comprising:
a measuring unit configured to measure a movement of an eye to be inspected;
an acquiring unit configured to acquire an image of a fundus of the eye to be inspected;
a control unit configured to control an acquiring position of the acquiring unit at a time of acquiring the image of the fundus; and
a predicting unit configured to predict the movement of the eye to be inspected based on a periodical movement of the eye to be inspected with respect to a fixation target, which movement has been measured by the measuring unit,
wherein the control unit controls the acquiring position based on the movement of the eye to be inspected which has been predicted by the predicting unit,
wherein the movement of the eye to be inspected with respect to the fixation target includes (a) a leaving movement in which a gazing position of the eye to be inspected leaves from the fixation target and (b) a returning movement in which the gazing position returns to the fixation target, and wherein the predicting unit predicts the movement of the eye to be inspected based on the leaving movement and the returning movement.

\* \* \* \* \*